(12) United States Patent
Cottrell et al.

(10) Patent No.: US 7,164,050 B2
(45) Date of Patent: Jan. 16, 2007

(54) PREPARATION OF HALO-OLEFIN

(75) Inventors: Stephen A. Cottrell, Baton Rouge, LA (US); William R. Jones, Baton Rouge, LA (US)

(73) Assignee: Honeywell International Inc., Morristown, NJ (US)

( * ) Notice: Subject to any disclaimer, the term of this patent is extended or adjusted under 35 U.S.C. 154(b) by 78 days.

(21) Appl. No.: 11/119,993

(22) Filed: May 2, 2005
(Under 37 CFR 1.47)

(65) Prior Publication Data
US 2005/0261528 A1 Nov. 24, 2005

Related U.S. Application Data

(60) Provisional application No. 60/567,258, filed on May 1, 2004.

(51) Int. Cl.
*C07C 17/23* (2006.01)
(52) U.S. Cl. ............... 570/158; 570/155; 570/156; 570/157; 570/216; 570/230
(58) Field of Classification Search ............... 570/158, 570/157, 156, 155, 230, 216
See application file for complete search history.

(56) References Cited

U.S. PATENT DOCUMENTS

| 2,754,336 A | 7/1956 | Chernosky et al. |
| 3,505,416 A | 4/1970 | Davis et al. |
| 5,124,494 A | 6/1992 | Ishihara et al. |

FOREIGN PATENT DOCUMENTS

| EP | 0364103 | 4/1990 |
| EP | 0416615 | 3/1991 |
| EP | 0496446 | 7/1992 |

*Primary Examiner*—Elvis O. Price
(74) *Attorney, Agent, or Firm*—Erika S. Wilson

(57) ABSTRACT

A process for preparing a halo-olefin to minimize one or more side reactions which form at least one impurity, said process comprising contacting a halogenated hydrocarbon with a metal dehalogenating agent dissolved in a solvent under conditions sufficient to dehalogenate said halogenated hydrocarbon to produce a product stream comprising said halo-olefin and at least one impurity, said metal dehalogenating agent having an average particle size within a range of average particle sizes, said impurity concentration of said product stream being essentially constant within said range and increasing significantly below said range.

18 Claims, 1 Drawing Sheet

US 7,164,050 B2

PREPARATION OF HALO-OLEFIN

FIELD OF INVENTION

Figure 1:
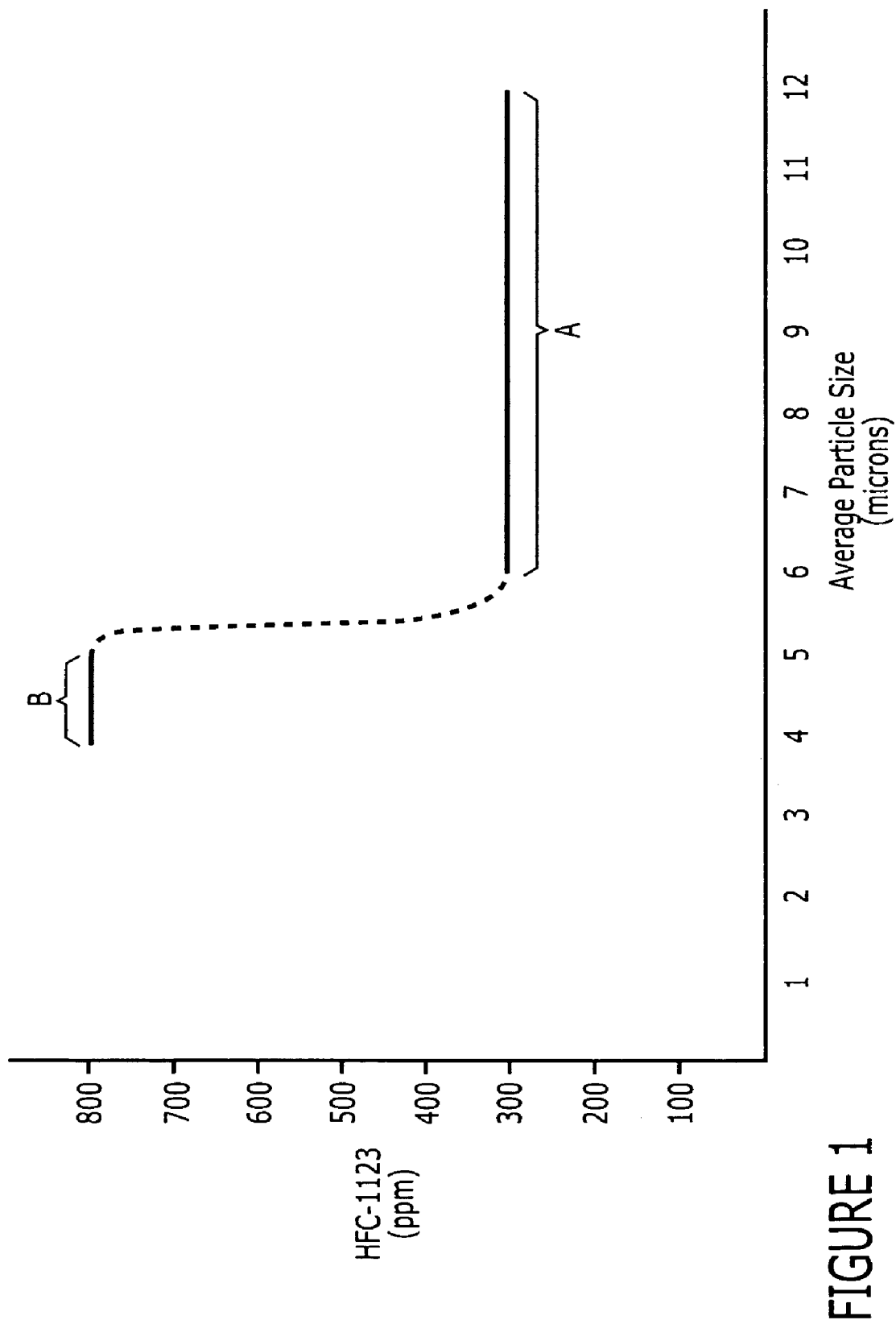

This invention relates to the dehalogenation of a halogen-containing compound. In one of its aspects, this invention relates to the dechlorination of a halogenated organic compound. In one of its more particular aspects, this invention relates to the dechlorination of trifluorotrichloroethane to produce chlorotrifluoroethylene.

BACKGROUND OF INVENTION

Intermediate compounds of significant industrial importance are prepared by the dehalogenation of saturated halocarbons. For example, polytrifluorochloroethylene is prepared by the polymerization of trifluorotrichloroethylene, an intermediate which is prepared by the dechlorination of trifluorotrichloroethane.

In a well known process, chlorotrifluoroethane (CTFE-1113) is produced by reacting a halogenated starting material, specifically, trichlorotrifluoroethane (CFC-113), with a metallic dehalogenation agent, such as zinc dust. (In this particular reaction, zinc chloride is produced as a co-product of the reaction). The zinc dust is dissolved/suspended in a solvent, such as methanol, which acts as a carrier for the zinc. Specifically, methanol is charged to an agitated vessel and then zinc dust is transferred to the methanol-containing vessel to create a slurry. This zinc/methanol slurry is then charged as a batch to an agitated reaction vessel in which CFC-113 is fed continuously in slight excess, thereby producing a vapor product stream.

The product stream consists mainly of CTFE-1113 and its major impurities 1,2-dichloro-1,1,2-trifluoroethane (HCFC-123a), trifluoroethene (HFC-1123), 1-chloro-2,2,2-trifluoroethane (CFC-133a), and unreacted CFC-113 and methanol. The CFC-113 and methanol are removed by distillation and recycled to the reactor. The remaining impurities are removed by multiple distillation steps and finally by sulfuric acid absorption and molecular sieve adsorption to reach the final product. The organic materials remaining in the reactor after the appropriate amount of CFC-113 has been fed to the zinc batch are flashed off and recovered for yield recovery. The remaining spent batch containing zinc chloride, methanol and unreacted zinc is discharged into a vessel for further processing. Specifically, the zinc chloride and methanol are processed in multiple distillation and vaporization steps after which the zinc chloride is pumped to final product storage and the methanol is recycled for use in future batches.

The unreacted zinc remains behind in the vessel and must be periodically removed as a solid waste stream. Typically, as much as 20% of the zinc may go unreacted in the process accounting for yield losses and significant costs to remove and dispose of the waste stream. Therefore, there is a need to reduce the amount of unreacted zinc and impurities such as HFC-1123. The present invention fulfills this need among others.

SUMMARY OF INVENTION

It is generally recognized that reducing the particle size of the agent increases its effective surface area and thereby improves yield. Contrary to conventional wisdom, applicants discovered that reducing the particle size of the agent past a certain point results in no appreciable increase in conversion rate, but increases instead the rate of side reactions, particularly those involving two or more steps. The increase in side reactions and the impurities they form makes meeting product quality specifications difficult, and increases distillation yield losses.

Without being bound to any particular theory for this discovered phenomenon, applicants suspect that the side reactions, particularly those involving two or more steps, benefit from an agent with increased surface area more so than the primary dehalogenation reaction. In other words, multi-step side reactions are more sensitive to changes in the effective surface area of the agent than is the primary reaction. The present invention exploits this differential in particle-size sensitivity between the main reaction and the side reactions. By sizing the agent to be no smaller than required to achieve an acceptable yield, the side reactions can be minimized, thereby decreasing waste.

In addition to minimizing side reactions, it has been found that using an agent with a slightly larger particle than would normally be used improves the overall processability of the agent and reactants. That is, by way of contrast, lower sizes of particles tend to result in increased handling difficulties due to the tendency of the material to "clump," thereby resulting in process downtime due to plugged piping and vessels.

Applicants have also discovered that certain economies can be realized by using an agent with larger than normal particle sizes since there is typically a premium paid for smaller particle agents. For example, with respect to zinc, sizes above 5 microns may not be considered premium quality since they are not suitable for pigments in paints and, thus, are less expensive.

Accordingly, one aspect of the present invention is a process for preparing a halo-olefin by dehalogenation using an agent having an average particle size which is small enough to provide for adequate yield but is not so small that it promotes side reactions over the main dehalogenation reactions. In a preferred embodiment, the process comprises: contacting a halogenated hydrocarbon with a metal dehalogenating agent dissolved in a solvent under conditions sufficient to dehalogenate the halogenated hydrocarbon to produce a product stream comprising the halo-olefin and impurities, the metal dehalogenating agent having an average particle size within a range of average particle sizes, the concentration of the impurities in the product stream being essentially constant for an average particle size within the range and increasing significantly for an average particle size below the range.

Another aspect of the invention is a process directed at producing CFC-113 with a minimum production of HFC-1123 by using an agent with a particle size that is small enough to provide for adequate yield but is not so small that it promotes side reactions over the main dehalogenation reactions. In a particularly preferred embodiment, the process comprises contacting CFC-113 with zinc particles dissolved in a solvent under conditions sufficient to dehalogenate the CFC-113 to produce CTFE-1113, the zinc particles having an average particle size of greater than about 5 microns.

DETAILED DESCRIPTION OF PREFFERED EMBODIMENT

According to the present invention, a process for preparing a halo-olefin is disclosed to minimize one or more side reactions which form at least one impurity. In a preferred embodiment, the process comprises contacting a halogenated starting material with a metal dehalogenating agent dissolved in a solvent under conditions sufficient to dehalogenate the halogenated starting material to produce a product stream comprising the halo-olefin and impurities. The metal dehalogenating agent has an average particle size within a range of average particle sizes, wherein the impurity concentration of the product stream is essentially constant within this range and increases significantly below this range.

In another preferred embodiment, the process comprises producing CFC-113 with a minimum production of HFC-1123 by using an agent with a particle size that is small enough to provide for adequate yield but is not so small that it promotes side reactions over the main dehalogenation reactions. In a particularly preferred embodiment, the process comprises contacting CFC-113 with zinc particles dissolved in a solvent under conditions sufficient to dehalogenate the CFC-113 to produce CTFE-1113, the zinc particles having an average particle size of greater than about 5 microns.

As herein used, the term "halogenated starting material" refers to any halogenated hydrocarbon or halocarbon which contains at least three halogen atoms per molecule, and which, when undergoing one dehalogenation, produces a halo-olefin containing at least one halogen atom per molecule. As used herein, a "halogenated hydrocarbon" is defined as a compound of carbon, hydrogen and halogen with any degree of saturation. The halogens preferably are selected from fluorine and chlorine. As used herein, a "halocarbon" is defined as halogenated hydrocarbon compounds consisting substantially exclusively of carbon and halogen with any degree of saturation. Preferred halogenated starting materials include trichlorotrifluoroethane (CFC-113), trichloroethane, dichlorodifluoroethane, and dichlorotetrafluoroethane. Most preferably, the starting material is CFC-113, which is commercially available from Honeywell (Morristown, N.J.).

A "halo-olefin," as used herein, is defined as an unsaturated halocarbon or halogenated hydrocarbon, with any degree of unsaturation, having no more than one chlorine atom per atom of carbon. Preferred halo-olefins include chlorotrifluoroethylene (CTFE-1113) produced from trifluorotrichloroethane, vinyl chloride produced from trichloroethane, difluoroethylene produced from dichlorodifluoroethane, and tetrafluoroethylene produced from dichlorotetrafluoroethane. Most preferably, the halo-olefin is CTFE-1113.

A number of well-known metallic dehalogenating agents may be used such as, tin, magnesium, iron, zinc, and aluminum. Zinc is a preferred dehalogenating agent. Such agents are commercially available from numerous sources including US Zinc (Houston, Tex.). Typically, suppliers of the agents offer them in various grades and particle sizes. As used herein, the term "average particle size" or "particle size" refers to the average diameter of the particles and is determined by means well known in the art. As mentioned above, the particle size of the agent is of critical importance in this invention and is discussed in greater detail below.

Preferably the agent is mixed with a solvent to form either a non-homogeneous or homogeneous mixture. Various solvents may be used, but in general, the solvent should be miscible with the halogenated starting material and also must be capable of dissolving the metal halide which is formed in the dehalogenation reaction by the metallic dehalogenating agent. Suitable solvents include methanol and ethanol. Methanol is a particularly preferred solvent.

The halogenated starting material can be dehalogenated, under suitable conditions, in the presence of a solvent and a metallic dehalogenating agent to produce halo-olefins. These conditions are well known and are described, for example, in U.S. Pat. Nos. 2,754,336 and 5,124,494, both of which are hereby incorporated by reference. For illustrative purposes, the practice of the present invention will be described in terms of the dechlorination of trifluorotrichloroethane to produce chlorotrifluoroethylene. It should be understood, however, that the process of this invention may be applied equally well to the production of any halo-olefin. For example, trichloroethane may be dehalogenated to vinyl chloride, dichlorodifluoroethane to difluoroethylene and dichlorotetrafluoroethane to tetrafluoroethylene.

The process of this invention is applicable to either continuous or batch type operations. In a continuous operation, a portion of the bottoms or "slurry" is introduced into the dehalogenation zone to initiate the reaction. The slurry is admixed with the material to be dehalogenated, the metal dehalogenation agent and the solvent prior to, simultaneously with, or subsequent to the addition of one or more of the above-indicated components of the process. The slurry is preferably admixed prior to the addition of the material to be dehalogenated by any convenient means.

In a bomb or batch type of operation, the slurry is introduced into the dehalogenation zone to initiate the reaction. The slurry is admixed with the material to be dehalogenated, the metal dehalogenation agent and the solvent prior to, simultaneously with, or subsequent to the addition of one or more of the components of the process. The slurry is preferably admixed prior to the addition of the material to be dehalogenated by any convenient means.

The applicants have discovered unexpectedly that the size range of the particles is important in optimizing yield. Specifically, applicants discovered that reducing particle size below a certain lower limit results in no appreciable increase in conversion rate, but rather increases the rate of side reactions, particularly those involving two or more steps. Likewise, applicants have discovered that increasing particle size above a certain upper limit results in diminished yield without a corresponding reduction in impurity formation. Therefore, applicants submit that optimum results can be obtained by using an agent having an average particle size which lies between these lower and upper limits, herein referred to as the "particle size range." In the following description of these upper and lower limits, reference is made to "impurities." Used in this context, the term "impurities" refers to impurities formed through a two-step reaction. An example of such an impurity is HFC-1123.

The lower limit of the range of average particle sizes can be ascertained by reference to a plot of average particle size versus impurity concentration as shown in FIG. 1. This plot is particular to the preparation of CFC-113 in which one or more side reactions form at least HFC-1123 as an impurity, although, as mentioned above, the present invention is not limited to this particular reaction. The plot shows two distinct portions, portion A in which the impurity concentration is low, and portion B in which it is much higher. At the time this application was prepared, there was no data available for the impurity concentration for an average particle size between portions A and B, although applicants suspect an exponential increase as indicated by the dotted line.

With respect to portion A, the HFC-1123 impurity concentrations are essentially constant. Stated alternatively, in portion A, the HFC-1123 impurity concentrations vary by no more than +/−15% from a mean impurity concentration value. In this particular plot, the impurity concentrations along portion A vary by no more than 10%. The lower limit of portion A defines the lower limit of the range in one embodiment. In this embodiment, the lower limit is greater than 5 microns, and preferably about 6 microns.

Portion B of the plot of FIG. 1 illustrates an exponential increase in HFC-1123 impurity concentration. Specifically, the HFC-1123 impurity concentration increases significantly and unexpectedly from 300 ppm at an average particle size of 6 microns, to 800 ppm at an average particle size of 5 microns. Without being bound to any particular theory for this discovered phenomena, applicants suspect that the side reactions are more sensitive to changes in the effective surface area of the agent than the primary dehalogenation reaction. In another embodiment, the lower limit of the range may be defined as being above portion B. The present invention exploits this differential in particle-size sensitivity between the main reaction and the side reactions. By sizing the agent to be no smaller than required to achieve an acceptable yield, the side reactions can be minimized thereby decreasing waste. For example, in the production of CFC-113 shown in FIG. 1, it has been found that an agent with an average particle size of greater than about 5 microns results in excellent yield with a minimum production of HFC-1123.

The upper limit of the range is the point above which there is a substantial decrease in the yield of the halo-olefin. As used in this context, the term "substantial" will largely depend on the economics of the process in the sense that above this point the reaction is no longer economically attractive. Since different producers may have different economic constraints, it is anticipated that the upper limit will vary. Nevertheless, it is generally recognized that a decrease in yield of about 5% from the mean yield of the range is considered substantial. In the production of CFC-113 a drop in yield from 87% to 82% (a decrease of about 6%) at an average particle size of about 12 microns is considered substantial. Therefore, the upper limit in this embodiment is less than about 12 microns.

For purposes of illustration herein, the lower limit of the average particle size range is denoted as "x" and the upper limit is denoted as "y." As mentioned above, the lower limit x is defined as the point below which there is a significant increase in the formation of an impurity, where the concentration of the impurity formed for average particle sizes within the range is essentially constant, and the upper limit y is defined as the point above which there is a substantial decrease in the formation of the halo-olefin, where the yield of the halo-olefin formed for average particle sizes within the range is essentially constant. Preferably, $x \leq 2y$, and more preferably, $x \leq 1.5y$.

With respect to the lower limit of the average particle size range, in a preferred embodiment, a reduction in average particle size of about 25% below the lower limit of the size range increases the formation of the impurity by at least a factor of 1.5, more preferably by a factor of at least 2, and even more preferably by a factor of at least 2.5, when compared to the formation of the impurity for the range. In one preferred embodiment, a reduction in average particle size of about 25% below the lower limit of the size range results in no significant increase in the formation of the halo-olefin. In one preferred embodiment, the lower limit of the average particle size range is greater than about 5 microns, preferably about 6 microns and, more preferably, about 7 microns.

With respect to the upper limit, in a preferred embodiment, an increase in particle size of greater than about 25% above the upper limit of the size range decreases the formation of the halo-olefin by at least 5%. In one preferred embodiment, the upper limit of the average particle size range is less than about 12 microns, preferably about 8 microns and, more preferably, about 9 microns.

In light of the disclosure above, one particularly preferred embodiment of the invention is a process for preparing CTFE-1113 to minimize one or more side reaction by-products, such as HFC-1123. The process comprises contacting a CFC-113 with zinc particles dissolved in a solvent under conditions sufficient to dehalogenate the CFC-113 to produce CTFE-1113, the zinc particles having an average particle size of about 6 to 9 microns.

For purposes of illustrating the invention the following non-limiting examples are provided along with two comparative examples.

EXAMPLE 1

This example illustrates the high yield and relatively low formation of impurities realized by using an agent having average particle sizes within a preferred average particle size range.

1500 lbs of standard grade zinc dust from US Zinc (Houston, Tex.) with an average particle size of 7 microns was slurried with methanol through agitation with a zinc to methanol ratio of 1:3. The slurry was then charged to a 1000 gallon reaction vessel. The reactor was maintained at 150° F. and 22 psig. High purity CFC-113 from Honeywell (Morristown, N.J.) (99.9% pure) was added in excess at a rate of 2–3 gallons/min over 2–3 hours. The product CTFE-1113 and its impurities were recovered as product vapor stream and recovered using standard distillation. The conversion (yield) of the zinc dust was measured using the captured product amount and the amount of zinc charged to the batch. The conversion (yield) for the zinc was 87%. HFC-1123 was formed at the concentration of 300 ppm in the CTFE-1113, which met product specifications.

EXAMPLE 2

This example illustrates the high yield and relatively low formation of impurities realized by using an agent having average particle sizes within a preferred average particle size range.

This experiment was conducted essentially the same as Example 1, except the zinc dust had a particle size of 6 microns. This zinc dust was slurried with methanol and charged to a reaction vessel. CFC-113 was added in excess and product CTFE-1113 and its impurities were recovered as product. The conversion (yield) of the zinc dust was measured using the captured product amount and the amount of zinc charged to the batch. The conversion (yield) for the zinc was 87.5%. HFC-1123 was formed at the concentration of 300 ppm in the CTFE-1113, which met product specifications.

COMPARATIVE EXAMPLE 1

This example illustrates the reduction of yield of the halo-olefin without a proportional reduction in impurities when an agent is used having an average particle size above the upper limit of the preferred average particle size range.

This experiment was conducted essentially the same as Example 1, except the zinc dust had a particle size of 12 microns. This zinc dust was slurried with methanol and charged to a reaction vessel. CFC-113 was added in excess and product CTFE-1113 and its impurities were recovered as product. The conversion (yield) of the zinc dust was measured using the captured product amount and the amount of zinc charged to the batch. The conversion (yield) for the zinc was 82%. HFC-1123 was formed at the concentration of 300 ppm in the CTFE-1113, which met product specifications.

Thus, an average zinc particle size above the upper limit results in a drop in yield of CTFE-1113 while the formation of the HFC-1123 remains about the same.

COMPARATIVE EXAMPLE 2

This example illustrates the result of an increase in the formation of impurities without a proportional increase in formation of halo-olefin when an agent is used having an average particle size below the lower limit of the preferred average particle size range.

This experiment was conducted essentially the same as Example 1, except the zinc dust had a particle size of 4 microns. The zinc dust was slurried with methanol and charged to a reaction vessel. CFC-113 was added in excess and product CTFE-1113 and its impurities were recovered as product. The conversion (yield) of the zinc dust was measured using the captured product amount and the amount of zinc charged to the batch. The conversion (yield) for the zinc was 87%. HFC-1123 was formed at a concentration of 800 ppm, which was well above product specifications and above the range that existing distillation equipment could purify the CTFE-1113. Process line plugging in the zinc system was also noted during the trial.

Thus, an average zinc particle size below the lower limit results in an increase in the formation of HFC-1123 while the formation of the CTFE-1123 remains about the same.

What is claimed is:

1. A process for preparing a halo-olefin to minimize one or more side reactions which form at least one impurity, said process comprising: contacting a halogenated hydrocarbon with a metal dehalogenating agent dissolved in a solvent under conditions sufficient to dehalogenate said halogenated hydrocarbon to produce a product stream comprising said halo-olefin and at least one impurity, said metal dehalogenating agent having an average particle size within a range of average particle sizes, said impurity concentration of said product stream being essentially constant within said range and increasing significantly below said range.

2. The process of claim 1, wherein the percentage yield of said halo-olefin in said product stream is essentially constant within said range and decreases substantially above said range.

3. The process of claim 1, wherein an average particle size about 25% below the lower limit of said range increases the impurity concentration by at least a factor of 1.5 compared to the impurity concentration for said range.

4. The process of claim 1, wherein an average particle size about 25% below the lower limit of said range results in essentially no increase in the formation of said halo-olefin.

5. The process of claim 2, wherein an average particle size greater than about 25% above the upper limit of said range decreases the yield of said halo-olefin in said product stream by at least about 5%.

6. The process of claim 1, wherein said impurity is formed in a multi-step side reaction.

7. The process of claim 1, wherein the lower limit of said range is greater than about 5 microns.

8. The process of claim 2, wherein the upper limit of said range is about 9 microns.

9. The process of claim 1, wherein said range is about 7 to about 8 microns.

10. The process of claim 1, wherein said halogenated starting material is selected from the group consisting of trichlorotrifluoroethane (CFC-113), trichloroethane, dichlorodifluoroethane, and dichlorotetrafluoroethane.

11. The process of claim 1, wherein said halogenated starting material is trichlorotrifluoroethane.

12. The process of claim 1, wherein said halo-olefin is selected from the group consisting of chlorotrifluoroethylene, vinyl chloride, difluoroethylene, and tetrafluoroethylene.

13. The process of claim 1, wherein said halo-olefin is chlorotrifluoroethylene.

14. The process of claim 1, wherein said dehalogenating agent is selected from the group consisting of tin, magnesium, iron, zinc, and aluminum.

15. The process of claim 1, wherein said dehalogenating agent is zinc.

16. The process of claim 1, wherein said impurity is HFC-1123.

17. A process for preparing CFC 113 to minimize one or more side reactions producing at least HFC-1123, said process comprising: contacting a CFC 113 with zinc particles dissolved in a solvent under conditions sufficient to dehalogenate said CFC 113 to produce CTFE 1113, said zinc particles having an average particle size of greater than about 5 microns to about 9 microns.

18. The process of claim 17, wherein said zinc particles have an average particle size of about 7 to about 8 microns.

* * * * *